United States Patent [19]

Douglas et al.

[11] Patent Number: 5,032,393
[45] Date of Patent: Jul. 16, 1991

[54] DRUG ADSORBATES

[75] Inventors: Stephen J. Douglas; Fiona R. Bird, both of Welwyn, England

[73] Assignee: Glaxo Group Limited, England

[21] Appl. No.: 349,999

[22] Filed: May 10, 1989

[30] Foreign Application Priority Data

May 11, 1988 [GB] United Kingdom ............... 8811167
Jul. 7, 1988 [GB] United Kingdom ............... 8816185

[51] Int. Cl.$^5$ .................... A61K 31/74; A61K 31/34; A01N 43/08
[52] U.S. Cl. ........................ 424/79; 424/78; 514/974; 514/471
[58] Field of Search ................ 424/79, 78; 514/974, 514/471

[56] References Cited

U.S. PATENT DOCUMENTS

| | | | |
|---|---|---|---|
| 2,828,207 | 3/1958 | Fullhart | 424/79 |
| 2,970,053 | 1/1961 | Martin | 424/79 |
| 2,990,332 | 6/1961 | Keating | 514/100 |
| 3,138,525 | 6/1964 | Koff | 424/79 |
| 3,949,068 | 4/1976 | Polin | 424/79 |
| 4,585,790 | 4/1986 | Padfield et al. | 514/471 |
| 4,788,055 | 11/1988 | Fischer et al. | 424/79 |

FOREIGN PATENT DOCUMENTS 63-69038 9/1989 Japan.
1218102 1/1971 United Kingdom.

OTHER PUBLICATIONS

Linnell et al., Liq. Pharm. Prepn. Contg Ion Exchange Resin, 1961, & Pharm. Sci. 25169.

Primary Examiner—John Doll
Assistant Examiner—Pili Curtis
Attorney, Agent, or Firm—Bacon & Thomas

[57] ABSTRACT

The bitter taste of ranitidine may be masked by forming an adsorbate with a synthetic cation exchange resin. The adsorbate is particularly suitable for use in pharmaceutical compositions for oral administration such as chewable or suckable tablets, granules and aqueous or non-aqueous suspensions.

13 Claims, No Drawings

DRUG ADSORBATES

The present invention relates to novel derivatives of ranitidine, a process for their preparation, and to their use in improved formulations of ranitidine, particularly for oral administration.

Ranitidine, N-[2-[[[5-(dimethylamino)methyl-2-furanyl]methyl]-thio]ethyl]-N'-methyl-2-nitro-1,1-ethenediamine, and its physiologically acceptable salts are described and claimed in British Patent Specification No. 1565966, and a particular crystalline form of ranitidine hydrochloride is described and claimed in British Patent Specification No. 2084580B. In both these specifications there is reference to formulations for oral administration, which may take the form of for example tablets, capsules, granules, powders, solutions, syrups, suspensions, or tablets or lozenges for buccal administration. Oral preparations of ranitidine are also disclosed in British Patent Specification No. 214280A.

Ranitidine is a potent histamine $H_2$-antagonist which, in the form of its hydrochloride salt, is widely used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

Oral administration constitutes a preferred route for administering ranitidine. Ranitidine, however, in common with many drug substances, has an inherently bitter taste, and this constitutes a disadvantage with certain types of oral preparation. Moreover, it is well known that patients may not complete a necessary course of medicine if they are prescribed an oral presentation which is particularly unpleasant to taste. The problems resulting from the bitter taste of ranitidine are particularly acute in formulations such as chewable tablets, granules, powders, solutions or suspensions. To some extent, the bitter taste may be masked by the use of sweetening and/or flavouring agents, although this is not entirely satisfactory, and an unpleasant after-taste may still remain in the mouth. In addition, there may be circumstances in which it is undesirable or inappropriate to use a sweetening and/or flavouring agent.

Various methods have been described for masking the bitter taste associated with drug substances, including the use of ion exchange resins, and the use of cation exchange resins has been described for masking the bitter taste of certain drugs containing amine or amide groups. Examples of such drugs include nicotinamide, diphenhydramine, dextromethorphan, chlorpheniramine and pseudoephedrine. The use of ion exchange resins has not, however, been described as a means of masking the bitter taste associated with $H_2$-receptor antagonists, including ranitidine.

We have now found that the taste of ranitidine may be satisfactorily masked by forming a complex with an ion exchange resin, to give a resin adsorbate which is substantially free of the bitter taste associated with ranitidine.

Thus, according to one aspect, the present invention provides a resin adsorbate for oral administration, which comprises a complex formed between ranitidine and a synthetic cation exchange resin.

According to a further aspect the invention provides a process for the preparation of a resin adsorbate of ranitidine which comprises contacting a synthetic cation exchange resin with ranitidine or a physiologically acceptable salt thereof.

According to yet another aspect, the invention provides a method of masking the taste of ranitidine which comprises contacting a synthetic cation exchange resin with ranitidine or a physiologically acceptable salt thereof, to give a resin adsorbate which is substantially free of the bitter taste associated with ranitidine.

The synthetic cation exchange resin may be for example a copolymer of styrene or acrylic or methacrylic acid with a vinyl aromatic compound such as divinylbenzene, and the resin may derive its exchange activity from either weakly or strongly acidic groups such as carboxylic acid or sulphonic acid groups. Examples of suitable resins are those that are copolymers of styrene and divinylbenzene which are sulphonated, or copolymers of methacrylic acid and divinylbenzene, including those available commercially as Dowex resins (available from Dow Chemical Company) or Amberlite resins (available from Rohm & Haas). The resin may be in either acid form or in the form of a salt with an alkali metal (e.g. sodium or potassium).

The resins used should be non-toxic and pharmaceutically acceptable.

Ranitidine may be employed in forming the adsorbate according to the invention in the form of either its free base or a physiologically acceptable salt. Such salts include salts with inorganic or organic acids such as the hydrochloride, hydrobromide, sulphate, acetate, maleate, succinate, fumarate and ascorbate salts. A particularly preferred salt for use according to the invention is the hydrochloride.

Examples of adsorbates according to the invention are those formed by contacting a salt of ranitidine, more particularly the hydrochloride, with a sulphonated styrene-divinylbenzene resin in salt form, more particularly the sodium salt (e.g. Amberlite IRP-69), or with a methacrylic acid-divinylbenzene resin in salt form, more particularly the potassium salt (e.g. Amberlite IRP-88); or ranitidine (free base) with a methacrylic acid-divinylbenzene resin in free acid form (e.g. Amberlite IRP-64).

Adsorbates formed from methacrylic acid-divinylbenzene resin in free acid form are particularly preferred. Such adsorbates may be formed by contacting the resin with ranitidine in the form of a salt (more particularly the hydrochloride) or, more preferably, with ranitidine free base.

Although all ratios of ranitidine to resin in the adsorbate are within the scope of the invention, the ranitidine content of the adsorbate may for example be in the range of 5% to 70% on a weight-to-weight basis, expressed in terms of the weight of ranitidine free base. The ranitidine content of the adsorbate is preferably 15% to 55%, more preferably 20% to 30%.

The resin adsorbate may be prepared by mixing the synthetic cation exchange resin with a solution of ranitidine free base or a salt thereof (more particularly ranitidine hydrochloride) in a suitable solvent, for example water. Alternatively a solution of ranitidine or a salt thereof may be passed through a column of the cation exchange resin.

The resin adsorbate may be incorporated into a pharmaceutical composition for oral administration, using one or more physiologically acceptable carriers or excipients.

Thus according to a further aspect, the invention provides a pharmaceutical composition, for oral use in human or veterinary medicine, comprising a resin adsorbate of ranitidine complexed with a synthetic cation exchange resin, which is formed by contacting a synthetic cation exchange resin with ranitidine or a physiologically acceptable salt thereof.

The amount of ranitidine in the oral formulation is preferably in the range of 50–600 mg, more preferably 50–400 mg, and in particular 150–300 mg, per dosage unit, expressed as the weight of free base. The unit dose may be administered, for example, one to four times daily, preferably once or twice. The exact dose will depend on the nature and severity of the condition being treated, and it will also be appreciated that it may be necessary to make routine variations in the dosage depending on the age and weight of the patient.

The compositions according to the invention may for example take the form of tablets, capsules, granules, powders, tablets or lozenges for buccal administration, or liquid preparations such as suspensions. Granules and powders may be ingested directly, or dispersed in water or other suitable vehicle prior to administration. Capsules may be of the hard or soft gelatin type, including chewable soft gelatin capsules.

Chewable or suckable tablets (including cast chewable tablets), chewable soft gelatin capsules, granules, and aqueous or non-aqueous suspensions represent particular dosage forms, of which chewable or suckable tablets, granules, and aqueous or non-aqueous suspensions are particularly preferred.

The compositions may be formulated using conventional carriers or excipients and well established techniques.

Thus for example, granules for direct ingestion or for reconstitution before administration may be prepared by granulating the resin adsorbate with a binding agent (e.g. polyvinylpyrrolidone or hydroxypropyl methylcellulose) and other suitable excipients such as fillers (e.g. sugars such as lactose, sucrose, dextrose, fructose and mannose, or sugar alcohols such as sorbitol, xylitol and mannitol). Tablets of the resin adsorbate may be obtained by compressing the granules with suitable tabletting aids such as lubricants (e.g. magnesium stearate) and additional binder. Cast chewable tablets may be prepared by incorporating the resin adsorbate in one or more low melting point fatty base(s) (e.g. triglyceride bases). Capsules may be prepared by dispersing the resin adsorbate in a suitable vehicle such as fractionated coconut oil and using standard equipment for the filling of soft and hard gelatin capsules.

Aqueous suspensions may be obtained by dispersing the resin adsorbate in a suitable aqueous vehicle such as water or aqueous alcohol (e.g. ethanol), optionally with the addition of suitable viscosity enhancing agent(s) (e.g. cellulose derivatives or xanthan gum). Non-aqueous suspensions may be obtained by dispersing the resin adsorbate in a suitable non-aqueous based vehicle, optionally with the addition of suitable viscosity enhancing agent(s) (e.g. colloidal silica, hydrogenated edible fats or aluminium stearate). Suitable non-aqueous vehicles include for example almond oil, arachis oil, soyabean oil or fractionated vegetable oils such as fractionated coconut oil. Preservative(s) (e.g. methyl, ethyl, propyl or butyl-hydroxybenzoates, sodium benzoate or sorbic acid) may be included as appropriate.

Aqueous based suspensions of the resin adsorbate may, if desired, be formed in situ by adding the resin to a solution of ranitidine or a physiologically acceptable salt thereof in a suitable aqueous vehicle or, more preferably, by adding water to a dry mix of the resin and the ranitidine or ranitidine salt in powder or granular form.

The various types of preparation may optionally contain bulk and/or intense sweeteners, flavouring agents and/or colouring agents as appropriate.

The pharmaceutical compositions according to the invention may be presented for single or multi-dose use. A single dose may for example be presented as a dry product comprising either the resin adsorbate or a mixture of the resin and the ranitidine or ranitidine salt (together with appropriate excipient(s)) contained in a sachet or other unit does container. The contents may then be added to water or another suitable vehicle before use. A single dose of a non-aqueous suspension may be presented as a ready constituted suspension in a suitably designed unit pack.

The following Examples A to E illustrate the preparation of resin adsorbates according to the invention.

Example A 10 g of Amberlite IRP-69 (a sulphonic acid resin in sodium salt form) was washed with water. A solution of ranitidine hydrochloride (20 g in 100 ml water) was added to the wet resin. The mix was agitated at room temperature for about 3 hours. The resin material was filtered off and washed, first with water and then with acetone. This was then dried by exposure to a dry atmosphere at room temperature. The dried resin adsorbate contained 37% ranitidine by weight and was substantially tasteless.

Example B

A solution of ranitidine free base (15 g) in distilled water (100 ml) was added to a stirred suspension of Amberlite IRP-64 (a carboxylic acid resin in free acid form) (35 g) in distilled water (150 ml). The mix was stirred at room temperature for 3 hours, and the solid was then collected and washed first with water and then with acetone. The product was dried under vacuum at room temperature. The dried resin adsorbate contained 27% ranitidine by weight and was substantially tasteless.

Example C

Approximately 200 g of Amberlite IRP-69 was suspended in distilled water (2 liters) and stirred for 30 minutes. Stirring was then discontinued and the suspension allowed to settle for 30 minutes. The liquid layer was discarded and the solids resuspended in a further 2 liters of distilled water. This stirring and settling procedure was repeated another four times.

The resin was then packed into a 9 cm diameter chromatography column. A solution of ranitidine hydrochloride (10% w/v) in distilled water was then passed through the column under gravity until the concentration of ranitidine hydrochloride added to the column was approximately equal to the concentration being eluted.

The drug resinate was removed from the column, washed with water (3×200 ml), absolute ethanol (3×200 ml) and dried under vacuum to yield a drug resinate containing 51% w/w ranitidine base equivalent, the taste of which was significantly improved as compared with ranitidine hydrochloride.

Example D

Ranitidine hydrochloride (300 g) was dissolved in distilled water (1 liter). This was added to Amberlite IRP-88 (a carboxylic acid resin in potassium salt form) (200 g) and the resulting suspension stirred at room temperature for 3 hours. Stirring was then discontinued and the solid allowed to settle for 2 hours. The liquid was discarded, the solid resuspended in distilled water (1 liter), stirred for 2 hours and then allowed to settle before discarding the liquid.

The solid was resuspended in distilled water (1 liter) containing ranitidine hydrochloride (300 g). After stirring for 3 hours, the solid was isolated by filtration, washed with distilled water (3×300 ml), washed with absolute ethanol (3×300 ml) and dried under vacuum. The resulting drug resinate contained 17% w/w ranitidine base equivalent, and was substantially tasteless.

Example E

Ranitidine hydrochloride (5.6 g) was dissolved in a solution of sodium hydroxide (0.64 g) in distilled water (100 ml). To this was added Amberlite IRP-64 (10 g) and the resulting suspension stirred at room temperature for 3 hours. The resin was found to have adsorbed 80% of the ranitidine hydrochloride from solution giving a drug resinate containing 28% w/w ranitidine base equivalent. The drug resinate was isolated by filtration, washed with water (3×30 ml) and absolute ethanol (3×30 ml), and dried under vacuum, giving a product which was substantially tasteless.

The following Examples 1 to 15 illustrate pharmaceutical compositions according to the invention in which the drug resinate is in particular the resin adsorbate described in the above Examples, more especially a ranitidine-Amberlite IRP-64 resinate. Other drug resinates formed by contacting other synthetic cation exchange resins with ranitidine or a physiologically acceptable salt thereof may be formulated in a similar manner.

| Drug resinate* | 50 g. |
|---|---|
| Xylitol | 144 g. |
| Peppermint flavour | 1 g. |
| Hydroxypropyl methylcellulose | 5 g. |

*containing 25% w/w ranitidine base equivalent

The drug resinate, xylitol and peppermint flavour were mixed together, granulated using a solution of the hydroxypropyl methylcellulose in aqueous ethanol, and then dried.

Example 2 Chewable or Suckable Tablet

The granulated material prepared in (a) above is compressed into tablets using a suitable tablet press fitted with appropriate punches.

Example 3 Chewable Tablet

| Drug resinate* | 6.72 g |
|---|---|
| Mannitol | 16.2 g |
| Aspartame | 0.5 g |
| Spearmint flavour | 0.25 g |
| Polyvinylpyrrolidone | 1.25 g |
| Magnesium stearate | 0.063 g |

*containing 22.3% w/w ranitidine base equivalent

All the powders except for the magnesium stearate were mixed together to give a uniform mixture. The magnesium stearate was then added and the powders mixed for a short time. The mixture was then compressed to give tablets of total weight approximately 2.5 g, each containing 150 mg ranitidine base equivalent.

Example 4 Aqueous Suspension

| Drug resinate* | 100 g. |
|---|---|
| Hydroxypropyl methylcellulose | 5 g. |
| Peppermint flavour | 5 g |
| Saccharin | 0.3 g |
| Sorbitol solution B.P.C. | 100 g |
| Propyl hydroxybenzoate | 0.15 g |
| Butyl hydroxybenzoate | 0.075 g |
| Purified water | to 1000 ml |

The drug resinate is dispersed in a solution of the hydroxypropyl methylcellulose in purified water containing the other components of the formulation, and the resultant suspension is adjusted to volume and mixed well.

Example 5 Aqueous Suspension

| Drug resinate* | 12 g |
|---|---|
| Xanthan gum | 0.2 g |
| Avicel RC591** | 1.5 g |
| Sodium saccharin | 0.1 g |
| Propyl hydroxybenzoate | 0.15 g |
| Butyl hydroxybenzoate | 0.075 g |
| Peppermint flavour | 0.5 g |
| Titanium dioxide | 0.2 g |
| Ethanol | 7.5 ml |
| Sorbitol solution BPC | 10 g |
| Purified water | to 100 ml |

*containing 25% w/w ranitidine base equivalent.
**mixture of 89% w/w microcrystalline cellulose and 11% w/w sodium carboxymethylcellulose.

The sodium saccharin was dissolved in the bulk of the water, and the xanthan gum and Avicel RC591 were added with vigorous mixing. The hydroxybenzoates and flavour were dissolved in the ethanol and added to the mixture, followed by the sorbitol solution, titanium dioxide and drug resinate. The resulting suspension was made up to volume with water, and mixed using a high shear mixer, to give a homogenous suspension.

Example 6 Aqueous Suspension in which the drug resinate is formed in situ.

| Ranitidine hydrochloride | 33.6 g |
|---|---|
| Amberlite IRP-69 resin | 200 g |
| Hydroxypropyl methylcellulose | 5 g |
| Peppermint flavour | 5 g |
| Saccharin | 0.3 g |
| Sorbitol solution B.P.C. | 100 g |
| Propyl hydroxybenzoate | 0.15 g |
| Butyl hydroxybenzoate | 0.075 g |
| Purified water | to 1000 ml |

The ranitidine hydrochloride is dissolved in a solution of the hydroxypropyl methylcellulose in purified water containing the other components of the formulation. The resin is added, and the resultant suspension is adjusted to volume and mixed well.

Example 7 Reconstitutable Aqueous Suspension

| Drug resinate* | 12.0 g |
|---|---|
| Xanthan gum | 0.2 g |

| -continued | |
|---|---|
| Avicel RC591** | 1.5 g |
| Sodium saccharin | 0.3 g |
| Sorbic acid | 0.2 g |
| Sodium methylhydroxybenzoate | 0.12 g |
| Sodium propylhydroxybenzoate | 0.08 g |
| Peppermint flavour | 0.5 g |
| Titanium dioxide | 0.2 g |
| Sorbitol powder | 20 g |

*containing 25% w/w ranitidine base equivalent
**mixture of 89% w/w microcrystalline cellulose and 11% w/w sodium carboxymethylcellulose All the powders were blended together using a suitable mixer for subsequent filling into a 150 ml bottle. At the time of dispensing, 80 ml of potable water is added and the mixture shaken to give 100 ml of suspension containing 150 mg ranitidine base equivalent per 5 ml.

Example 8 Reconstitutable Aqueous Suspension in which the drug resinate is formed in situ

| Ranitidine free base | 3 g |
|---|---|
| Amberlite IRP-64 | 4 g |
| Xanthan gum | 0.2 g |
| Avicel RC591* | 1.5 g |
| Sodium saccharin | 0.3 g |
| Sorbic acid | 0.2 g |
| Sodium methylhydroxybenzoate | 0.12 g |
| Sodium propylhydroxybenzoate | 0.08 g |
| Peppermint flavour | 0.5 g |
| Titanium dioxide | 0.2 g |
| Sorbitol powder | 20 g |

*mixture of 89% w/w microcrystalline cellulose and 11% w/w sodium carboxymethylcellulose Example 9 Reconstitutable Aqueous Suspension in which the drug resinate is formed in situ

| Ranitidine hydrochloride | 3.36 g |
|---|---|
| Amberlite IRP-64 | 4.0 g |
| Sodium hydrogen carbonate | 0.8 g |
| Xanthan gum | 0.2 g |
| Avicel RC591* | 1.5 g |
| Sodium saccharin | 0.3 g |
| Sorbic acid | 0.2 g |
| Sodium methylhydroxybenzoate | 0.12 g |
| Sodium propylhydroxybenzoate | 0.08 g |
| Peppermint flavour | 0.5 g |
| Titanium dioxide | 0.2 g |
| Sorbitol powder | 20 g |

*mixture of 89% w/w microcrystalline cellulose and 11% w/w sodium carboxymethylcellulose Method as in Example 7.

Example 10 Reconstitutable Unit Dose Aqueous Suspension

| Drug resinate* | 0.6 g |
|---|---|
| Xanthan gum | 20 mg |
| Peppermint flavour | 10 mg |
| Aspartame | 20 mg |
| Xylitol | 2 g |

*containing 25% w/w ranitidine base equivalent

The powders were blended together using a suitable mixer and filled into a unit dose container. The dose is prepared by emptying the powder into about 20 ml of potable water and stirring for 30 seconds.

Alternative sugars such as sorbitol, mannitol, dextrose or sucrose may be used in place of xylitol. Alternative intense sweeteners such as sodium saccharin, cyclamate, thaumatin and acesulfam K may be used in place of aspartame.

Example 11 Reconstitutable Unit Dose Aqueous Suspension in which the drug resinate is formed in situ

| Ranitidine base | 0.15 g |
|---|---|
| Amberlite IRP-64 | 0.2 g |
| Xanthan gum | 20 mg |
| Peppermint flavour | 10 mg |
| Aspartame | 20 mg |
| Xylitol | 2 g |

Method as in Example 10.

Example 12 Reconstitutable Unit Dose Aqueous Suspension in which the drug resinate is formed in situ

| Ranitidine hydrochloride | 0.168 g |
|---|---|
| Amberlite IRP-88 | 0.2 g |
| Xanthan gum | 20 mg |
| Peppermint flavour | 10 mg |
| Aspartame | 20 mg |
| Xylitol | 2 g |

Method as in Example 10.

Example 13 Non-Aqueous Suspension

| Drug resinate* | 12 g |
|---|---|
| Aspartame | 1 g |
| Peppermint flavour | 0.5 g |
| Xylitol | 15 g |
| Colloidal silica | 0.2 g |
| Fractionated coconut oil to | 100 ml |

*containing 25% w/w ranitidine base equivalent

The drug resinate and xylitol were dispersed in the bulk of the fractionated coconut oil by high shear mixing. The remaining ingredients were added and mixed in using a suitable mixer. The suspension was made up to volume with fractionated coconut oil and mixed well. Each 5 ml of suspension contains 150 mg ranitidine base equivalent.

Alternative sugars such as mannitol, sorbitol, sucrose or dextrose may be used in place of xylitol. Other suitable oils such as arachis oil or soyabean oil may be used in place of fractionated coconut oil.

Example 14 Chewable Soft Gelatin Capsule

| | per capsule |
|---|---|
| Drug resinate* | 0.6 g |
| Aspartame | 20 mg |
| Flavour | qs |
| Fractionated coconut oil | 0.8 g |

*containing 25% w/w ranitidine base equivalent

The drug resinate and other powders are dispersed in the fractionated coconut oil using a suitable high shear mixer and the resulting suspension filled into chewable soft gelatin capsules. Each capsule contains 150 mg ranitidine base equivalent.

Example 15 Cast Chewable Tablet

|  | per tablet |
|---|---|
| Drug resinate* | 0.6 g |
| Aspartame | 0.01 g |
| Flavour | 0.005 g |
| Theobroma oil | 0.36 g |
| Witepsol HI5** | 1.8 g |

*containing 25% w/w ranitidine base equivalent
**Triglyceride suppository base manufactured by Dynamit Nobel.

The Witepsol HI5 and theobroma oil were melted together and heated to 36° C. The solids were incorporated and the molten mixture cast into tablet shaped moulds. After solidification the tablets were removed, each tablet containing 150 mg ranitidine base equivalent.

We claim:

1. A resin adsorbate which comprises a complex formed between ranitidine and a synthetic cation exchange resin, wherein said syntheticati on exchange resin is selected from copolymer of styrene and divinylbenzene which are sulphonated, and copolymers of methacrylic and divinylbenzene.

2. A resin adsorbate according to claim 1 in which said synthetic cation exchange resin is in acid form or is in the form of a salt with an alkali metal.

3. A resin adsorbate according to claim 1 in which said synthetic cation exchange resin is a methacrylic aciddivinylbenzene resin in free acid form.

4. A resin adsorbate according to claim 1 containing 5 to 70% ranitidine expressed as the weight of ranitidine free base based on the weight of resin adsorbate.

5. A resin adsorbate according to claim 5 containing 20 to 30% of ranitidine.

6. A resin adsorbate according to claim 5 containing 15 to 55% ranitidine.

7. A resin adsorbate according to claim 4 containing 5 to 70% ranitidine expressed as the weight of ranitidine free base based on the weight of resin adsorbate.

8. A resin adsorbate according to claim 8 containing 20 to 30% ranitidine.

9. A resin adsorbate according to claim 8 containing 15 to 55% ranitidine.

10. A resin adsorbate according to claim 1 which is substantially free of the bitter taste associated with ranitidine.

11. A resin adsorbate according to claim 4 which is substantially free of the bitter taste associated with ranitidine.

* * * * *

UNITED STATES PATENT AND TRADEMARK OFFICE
CERTIFICATE OF CORRECTION

PATENT NO. : 5,032,393
DATED : July 16, 1991
INVENTOR(S) : DOUGLAS et al.

It is certified that error appears in the above-identified patent and that said Letters Patent is hereby corrected as shown below:

Col. 9
Claim 1, line 3, please delete "syntheticati on" and insert --synthetic cation--;

line 4, please delete "copolymer" and insert --copolymers--;

Col. 10,
  Claim 3, line 3, please delete "aciddivinylbenzene" and insert --acid-divinylbenzene--.

Claim 5, line 1, please delete "5" and insert --4--.

Claim 6, line 1, please delete "5" and insert --4--.

Claim 7, line 1, please delete "4" and insert --3--.

Claim 8, line 1, delete "8" and insert --7--.

Signed and Sealed this

First Day of June, 1993

Attest:

MICHAEL K. KIRK

Attesting Officer      Acting Commissioner of Patents and Trademarks

UNITED STATES PATENT AND TRADEMARK OFFICE
CERTIFICATE OF CORRECTION

PATENT NO. :    5,032,393

DATED       :    July 16, 1991

INVENTOR(S) :    Stephen J. DOUGLAS et al.

It is certified that error appears in the above-identified patent and that said Letters Patent is hereby corrected as shown below:

Column 9, claim 1, line 6, please insert --acid-- after 'methacrylic'.

Signed and Sealed this

Fifth Day of July, 1994

Attest:

BRUCE LEHMAN

*Attesting Officer*          *Commissioner of Patents and Trademarks*